(12) United States Patent
Wakabayashi

(10) Patent No.: US 7,038,459 B2
(45) Date of Patent: May 2, 2006

(54) OIL DETERIORATION DETECTION APPARATUS

(75) Inventor: Shinji Wakabayashi, Anjo (JP)

(73) Assignee: DENSO Corporation, Kariya (JP)

( * ) Notice: Subject to any disclaimer, the term of this patent is extended or adjusted under 35 U.S.C. 154(b) by 112 days.

(21) Appl. No.: 10/695,866

(22) Filed: Oct. 30, 2003

(65) Prior Publication Data

US 2004/0100291 A1     May 27, 2004

(30) Foreign Application Priority Data

Oct. 30, 2002    (JP)    .............................. 2002-316439

(51) Int. Cl.
*G01N 27/416*    (2006.01)
*G01N 27/02*    (2006.01)

(52) U.S. Cl. ....................... 324/438; 324/446; 340/652
(58) Field of Classification Search ................ 324/425, 324/444, 446, 439, 438–450; 204/401, 433, 204/400; 702/116; 340/514, 650–652, 659, 340/661–664, 457.4; 701/29–31
See application file for complete search history.

(56) References Cited

U.S. PATENT DOCUMENTS

| | | | | |
|---|---|---|---|---|
| 4,353,867 A | * | 10/1982 | Luzzana | 204/403.14 |
| 4,532,013 A | * | 7/1985 | Dietz et al. | 205/784 |
| 4,777,444 A | * | 10/1988 | Beijk et al. | 324/439 |
| 4,829,253 A | * | 5/1989 | Koluvek | 324/438 |
| 2002/0097053 A1 | * | 7/2002 | Tamagawa et al. | 324/382 |

FOREIGN PATENT DOCUMENTS

| | | |
|---|---|---|
| JP | 62-261950 | 11/1987 |
| JP | 2-309240 | 12/1990 |
| JP | 5-340787 | 12/1993 |
| JP | 8-8707 | 1/1996 |

* cited by examiner

*Primary Examiner*—Anjan Deb
*Assistant Examiner*—Jeff Natalini
(74) *Attorney, Agent, or Firm*—Nixon & Vanderhye P.C.

(57) ABSTRACT

An oil deterioration detection apparatus includes a sensor, an evaluation circuit, and a malfunction detecting circuit. The evaluation circuit has a determination circuit. The malfunction detecting circuit has a resistor and a switch. The evaluation circuit evaluates a condition of the oil based on a normal voltage. The normal voltage is measured when the switch is opened so that the resistor is not electrically conducted. The determination circuit determines whether the sensor malfunctions based on a relation between the normal voltage and a divided voltage. The divided voltage is measured when the switch is closed so that the resistor is electrically conducted in parallel with the sensor.

20 Claims, 4 Drawing Sheets

OIL DETERIORATION DETECTION APPARATUS

CROSS REFERENCE TO RELATED APPLICATIONS

This application is based on Japanese Patent Application No. 2002-316439 filed on Oct. 30, 2002, the contents of which are incorporated herein by reference.

BACKGROUND

1. Field of the Invention

The exemplary embodiments of the present invention relate to an oil deterioration detection apparatus.

2. Description of Related Art

There is an oil deterioration detection apparatus, which uses dipole electrodes to detect oil deterioration by a PH of oil. A reference electrode and a sensitive electrode are used as the dipole electrodes. The oil deterioration detection apparatus measures an electric potential difference between the reference electrode and the sensitive electrode.

The oil deterioration detection apparatus has an oil deterioration detection part and an electric circuit. The oil deterioration detection part includes an oil deterioration-detecting sensor. The oil deterioration-detecting sensor has the reference electrode and the sensitive electrode. The electric circuit includes an operational amplifier and so on that measures the electric potential difference between the reference electrode and the sensitive electrode.

The oil deterioration-detecting sensor is used as a signal output circuit that outputs a true value of the electric potential difference between the electrodes. The operational amplifier is used as an input circuit that inputs the true value of the electric potential difference.

When the oil is deteriorated, the output signal varies. As a result, the oil deterioration detection apparatus can evaluates the deterioration of the oil.

However, in the oil deterioration detection apparatus, even if the oil deterioration-detecting sensor itself malfunctions, it does not detect a malfunction condition of the sensor itself. This is because that the output signal from the oil deterioration-detecting sensor varies based on the deterioration of the oil, so that the deterioration detection apparatus merely evaluates that the oil is deteriorated when the output signal varies. In addition, the oil deterioration detection apparatus does not have a detection element that detects the malfunction condition of the sensor. Therefore, it is difficult for the oil deterioration detection apparatus to distinguish the deterioration of the oil and the malfunction of the sensor only from the output signal. As a result, the oil deterioration detection apparatus may misunderstand the condition of the oil if the sensor malfunctions.

In addition, if the sensor malfunctions due to a broken wire, it has a problem that the input signal of the amplifier cannot be defined within a predetermined voltage range of the amplifier. In such a situation, the input circuit (amplifier) may be broken, too.

By the way, JP-A-H08-008708 discloses an input protection circuit. The input protection circuit has a protection transistor that is connected to an input circuit. A control voltage is supplied to a gate of the protection transistor, and an input signal is inputted into a drain of the transistor. An output, which is subtracted the gate-source voltage from a power supply voltage, is outputted though a source of the transistor. According to the input protection circuit, a stable drive signal is supplied to the input circuit.

However, the input protection circuit is not used for the oil deterioration detection apparatus, and cannot apply to define the input signal of the amplifier of the oil deterioration detection apparatus when the electrodes malfunctions of the sensor due to a broken wire.

SUMMARY

A feature of an exemplary embodiment of the present invention is to provide an oil deterioration detection apparatus that can detect a malfunction of an oil deterioration-detecting sensor to prevent a detection of oil deterioration from having an error by mistake.

Another feature of an exemplary embodiment of the present invention is to provide the oil deterioration detection apparatus that is possible to be protected from being damaged.

According to one aspect of the present invention, an oil deterioration detection apparatus includes a sensor, a malfunction detecting circuit, an evaluation circuit, and a determination circuit. The sensor detects a characteristic of oil and produces a characteristic signal. The malfunction detecting circuit has a switch that is connected in parallel with the sensor. The evaluation circuit evaluates whether the oil is deteriorated or not based on the characteristic signal. The characteristic signal used in the evaluation circuit is detected when the switch is opened so that the malfunction detecting circuit is not electrically conducted in parallel with the sensor. The determination circuit determines whether the sensor malfunctions or not based on the characteristic signal. The characteristic signal used in the determination circuit is detected when the switch is closed so that the malfunction detecting circuit is electrically conducted in parallel with the sensor.

In the oil deterioration detection apparatus, according to an operation of the switch, different characteristic signals are measured with the evaluation circuit and the determination circuit. Accordingly, the oil deterioration detection apparatus can evaluate whether the oil is deteriorated or not, and it also can determine whether the sensor malfunctions.

In addition, in the oil deterioration detection apparatus, when the determination circuit determines that the sensor malfunctions, the switch is closed so that the malfunction detecting circuit is electrically conducted to a measurement circuit having an amplifier. Therefore, an input signal of the measurement circuit is defined with the malfunction detecting circuit, thereby preventing the measurement circuit from being damaged.

BRIEF DESCRIPTION OF THE DRAWINGS

The above and other objects, features and advantages of exemplary embodiments of the present invention will become more apparent from the following detailed description made with reference to the accompanying drawings. In the drawings.

DETAILED DESCRIPTION OF NON-LIMITING EXEMPLARY EMBODIMENTS.

The exemplary embodiments of the present invention will be explained with reference to the accompanying drawings.

Figure 1:
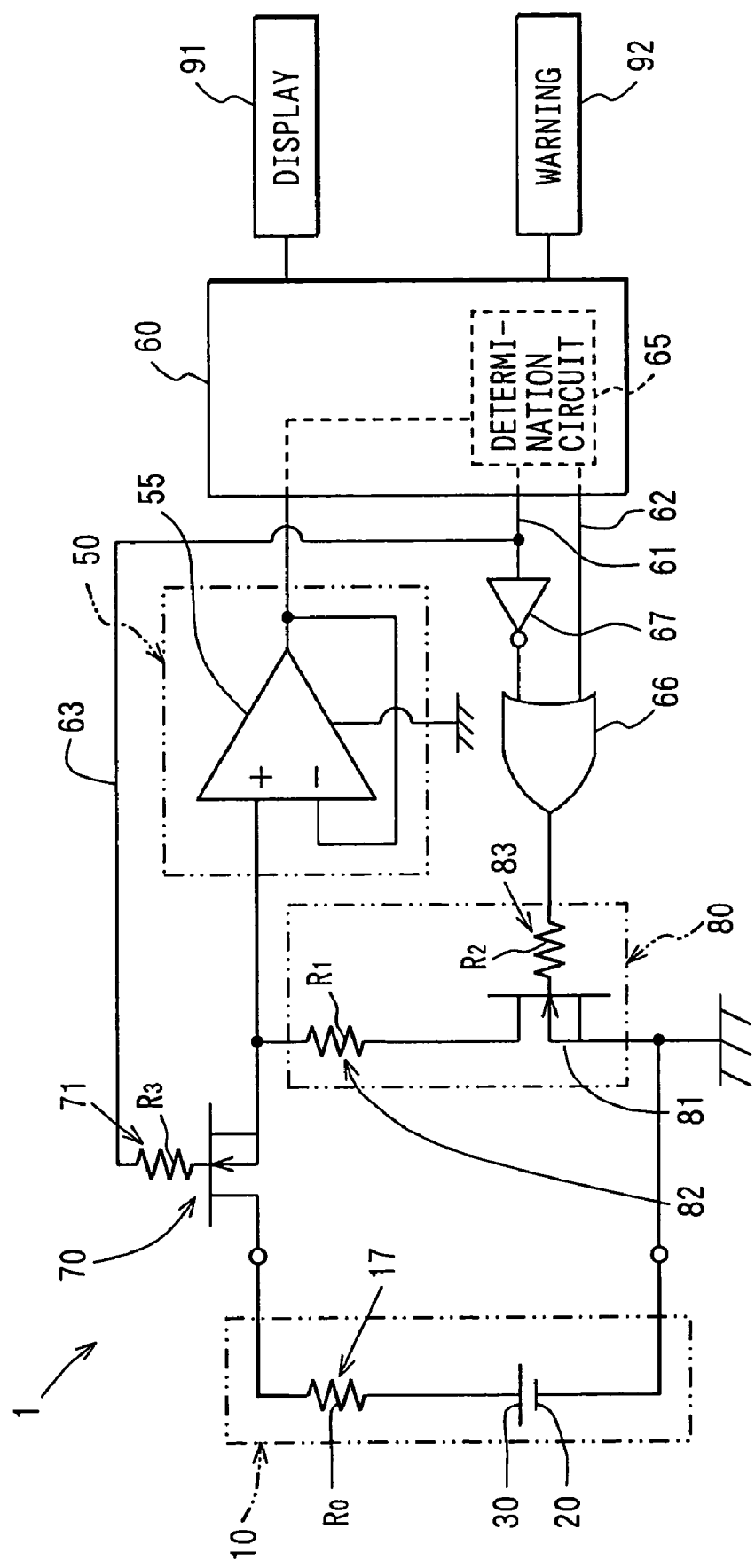
FIG. 1 is an electric circuit of an oil deterioration detector according to an embodiment of the present invention.
Figure 5A:
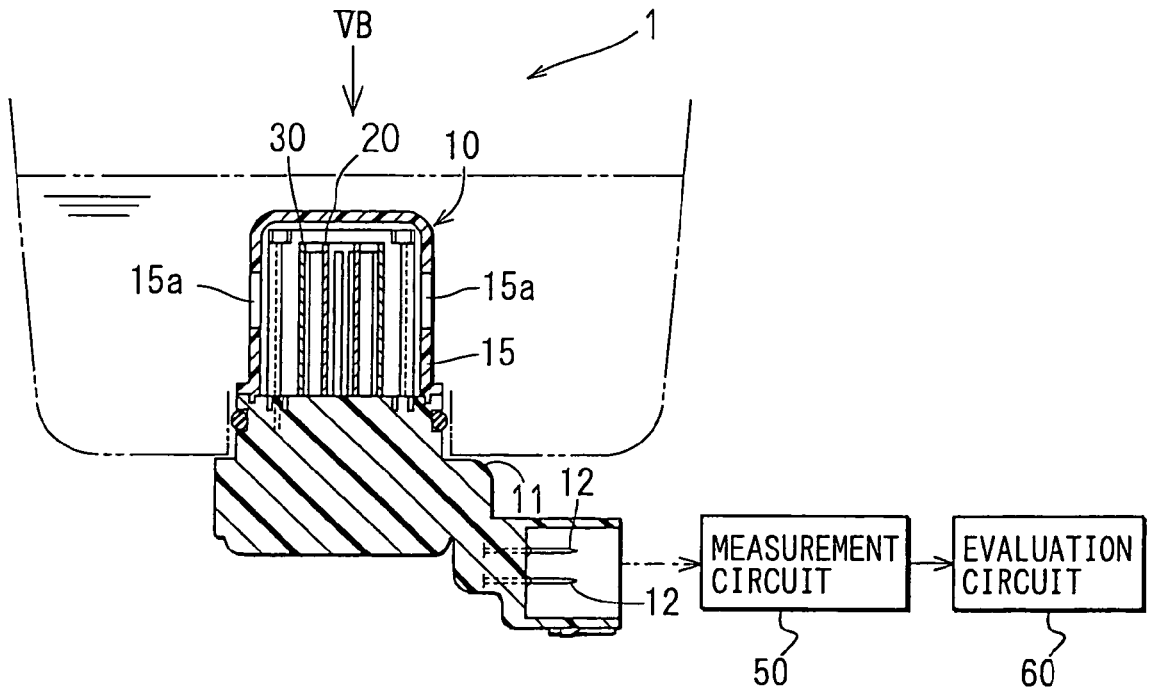
FIG. 5A is a cross-sectional view of the oil deterioration-detecting sensor according to the embodiment.

FIG. 1 shows an electric circuit of an oil deterioration detector 1 according to the present invention. The oil deterioration detector 1 is used for detecting a deterioration of oil. The oil deterioration detector 1 is disposed in an oil pan of a vehicle as shown in FIG. 5A. The oil deterioration detector 1 detects and evaluates a deterioration degree of oil. The oil is used as at least one of a hydraulic control oil and motor oil.

As shown in FIG. 1, the oil deterioration detector 1 has an oil deterioration detecting part 10, a measurement circuit 50, an evaluation circuit 60, connection switching circuits 66, 67, 70, a malfunction detecting circuit 80, a display 91, and a warning element 92. The connection switching circuits 66, 67, 70 have an OR-circuit 66, an inverter 67, and a second switch 70.

The oil deterioration detecting part 10 (hereinafter referred to as a deterioration-detecting sensor) detects a condition of the oil, and produces an oil deterioration detection signal. The oil deterioration-detecting sensor 10 has two electrodes, which are a first electrode 20 and a second electrode 30, to detect the condition of the oil. The first electrode 20 and the second electrode 30 have an interelectrode resistance Ro. The interelectrode resistance Ro is represented by an interelectrode resistor 17 in FIG. 1. The first electrode 20 is grounded.

The measurement circuit 50 has an amplifier, such as a difference input type operational amplifier 55. The operational amplifier 55 is connected to a power supply (Not shown) via a wire. The operational amplifier 55 is grounded via another wire. The operational amplifier 55 has a non-inverting input terminal (+), an inverting input terminal (−), and an output terminal. The non-inverting input terminal (+) is electrically connected to the oil deterioration-detecting sensor 10. The measurement circuit 50 receives the oil deterioration detection signal from the oil deterioration-detecting sensor 10 via the non-inverting input terminal (+). When the measurement circuit 50 receives the oil deterioration detection signal via the non-inverting input terminal (+), the operational amplifier 55 converts the signal with an impedance conversion.

The converted signal is outputted from the output terminal to the evaluation circuit 60 as a measurement voltage. The converted signal is also inputted into the inverting input terminal (−) via a feedback resistor. That is, the inverting input terminal (−) inputs a signal corresponding to the measurement voltage. Accordingly, the measurement circuit 50 amplifies and converts the oil deterioration detection signal with a predetermined amplification factor, and produces the measurement voltage. The measurement circuit 50 is electrically connected to the evaluation circuit 60.

The evaluation circuit 60 receives the measurement voltage from the measurement circuit 50. The evaluation circuit 60 evaluates the condition of the oil whether the oil is deteriorated based on the measurement voltage. The evaluation of the oil condition in the evaluation circuit 60 is carried out by a comparison of the measurement voltage and a threshold value. The evaluation circuit 60 produces a deterioration signal when the oil is deteriorated. The evaluation circuit 60 is electrically connected to the display 91 and the warning part 92.

The display 91 notifies the driver of the deterioration condition of the oil when the display 91 receives the deterioration signal from the evaluation circuit 60. A lamp and a buzzer may be used instead of the display 91. The lamp notifies the driver of the deterioration condition by blinking. The buzzer notifies the driver of the deterioration condition by sounding. The display 91, the lamp, or the buzzer is disposed at an instrument panel or a display for a navigation system.

The evaluation circuit 60 has a determination circuit 65. The determination circuit 65 determines whether the oil deterioration-detecting sensor 10 malfunctions. The determination circuit 65 is electrically connected to the malfunction detecting circuit 80 by a first wire. 61 and a second wire 62 via the OR-circuit 66 and the inverter 67. The determination circuit 65 is also connected to the second switch 70 by a third wire 63.

The determination circuit 65 sends a deterioration detecting enabling signal via the first and third wires 61, 63. The determination circuit also sends a malfunction detecting enabling signal via the second wire 62. The deterioration detecting enabling signal is sent when the oil deterioration detector 1 evaluates the condition of the oil. The malfunction detecting enabling signal is sent when the oil deterioration detector 1 determines whether the oil deterioration-detecting sensor 10 malfunctions or not. If the determination circuit 65 determines that the oil deterioration-detecting sensor 10 malfunctions, the determination circuit 65 produces a malfunction signal.

The warning part 92 designates the malfunction condition of the oil deterioration-detecting sensor 10 when the warning part 92 receives the malfunction signal. The display, the lamp, or the buzzer is used as the warning part 92.

The malfunction detecting circuit 80 is connected in parallel with the oil deterioration-detecting sensor 10. The malfunction detecting circuit 80 has a first switch 81, a first resistor 82, and a second resistor 83. The malfunction detecting circuit 80 can be electrically conducted with the oil deterioration-detecting sensor 10 or not by switching the first switch 81. That is, the first switch 81 switches the conduction of the malfunction detecting circuit 80.

The first switch 81 is made of a semiconductor, which is a field effect transistor (FET). The first switch 81 is grounded with a source terminal of the FET. The first switch 81 is connected to the first resistor 82 with a drain terminal of the FET. The first switch 81 is also connected to the OR-circuit 66 with a gate terminal of the FET via the second resistor 83. The second resistor 83 has a second resistance R2 to adjust a driving voltage of a driving signal so that the driving voltage is less than an allowable voltage of the first switch 81. The driving signal is outputted from the determination circuit 65 of the evaluation circuit 60 so that the first switch 81 is turned on (closed) or off (opened).

The first resistor 82 is connected to a terminal between the oil deterioration-detecting sensor 10 and the measurement circuit 50. The first resistor 82 has a first resistance R1.

In the connection switching circuits 66, 67, 70, each of the OR-circuit 66 and the inverter 67 is one of a logic circuit. The OR-circuit 66 is connected to the determination circuit 65 of the evaluation circuit 60 with two wires 61, 62 in its input side. The first wire 61 is electrically connected between the input side of the OR-circuit 66 and the determination circuit 65 via the inverter 67. The second wire 61 is directly connected between them.

The second switch 70 is made of a semiconductor, which is a FET. The second switch 70 is connected between the oil deterioration-detecting sensor 10 and the measurement circuit 50. The second switch 70 is also connected to a terminal between the inverter 67 and the determination circuit 65 with its gate terminal via a third resistor 71. The third resistor 71 has a third resistance R3 to adjust a driving voltage of the driving signal so that the driving voltage is less than an allowable voltage of the second switch 70. The second switch 70 can conduct the connection between the oil deterioration-detecting sensor 10 and the measurement circuit 50 or not.

Figure 5B:
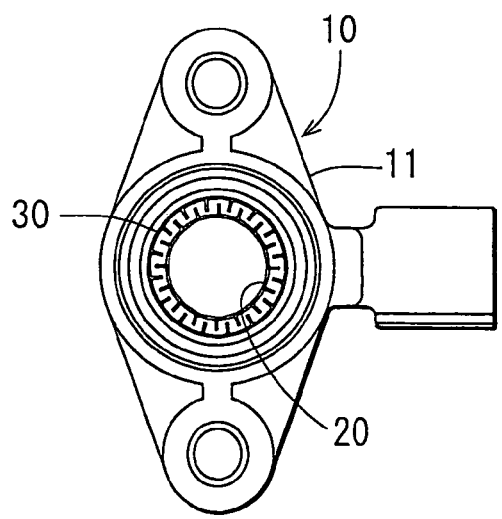
FIG. 5B is a top view of the oil deterioration-detecting sensor according to the embodiment.

As shown in FIGS. 5A–5B, the oil deterioration-detecting sensor 10 has a first electrode 20 and a second electrode 30. The first electrode 20 and the second electrode 30 are immersed in the oil within the oil pan of the vehicle. The first electrode 20 and the second electrode 30 are mounted on a support member 11 by adhesive. The support member 11 is made of an isolative resin. The support member 11 has terminals 12, 12, which are electrically connected to the first electrode 20 and the second electrode 30, respectively. A cover 15 is combined with the support member 11 to cover the first electrode 20 and the second electrode 30. The cover 15 has communicating holes 15a through which the oil flows inside and outside the cover 15.

The first electrode 20 and the second electrode 30 generate the oil deterioration detection signal based on electric potentials generated on each electrode 20, 30. Various electrodes are used as the electrodes 20, 30, such as battery-like structural electrodes, and capacitor-like structural electrodes. The battery-like structural electrodes have two electrodes that are made of two different metallic materials. The battery-like structural electrodes generate a potential difference between two electrodes when the electrodes are immersed in the oil. The capacitor-like structural electrodes accumulate capacitance between two electrodes when the electrodes are immersed in the oil.

In this embodiment, the battery-like structural electrodes are used as the electrodes 20, 30 of the deterioration-detecting sensor 10.

The first electrode 20 is made of a first metallic material. The first metallic material has a constant potential regardless of acidity or basicity in the oil. Hereinafter, the first electrode 20 is referred to as a reference electrode. The second electrode 30 is made of a second metallic material. The second metallic material changes its potential in response to the acidity or the basicity in the oil. Hereinafter, the second electrode 30 is referred to as a sensitive electrode.

Cobalt (Co), lead (Pb), zinc (Zn), or tin (Sn) is used as the first metallic material. Stainless (SUS), titanium (Ti), or tungsten (W) is used as the second metallic material.

In this embodiment, the first electrode 20 uses the cobalt (Co) as the first metallic material. The second electrode 30 uses the tungsten (W) as the second metallic material.

Each of the first electrode 20 and the second electrode 30 has approximately cylindrical shape as shown in FIGS. 3 to 5B. The second electrode 30 is coaxially disposed outside the first electrode 20. The first electrode 20 and the second electrode 30 are immersed in the oil within the oil pan of the vehicle.

Figure 3:
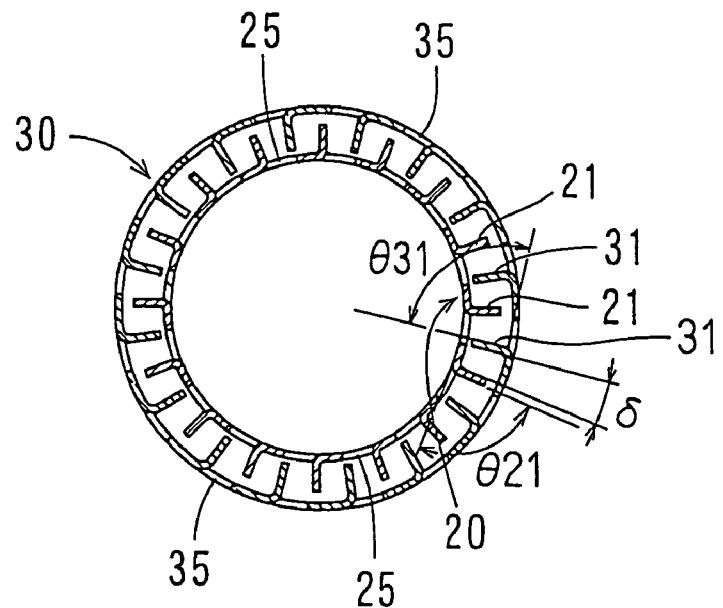
FIG. 3 is a sectional view of an oil deterioration-detecting sensor according to the embodiment.
Figure 4:
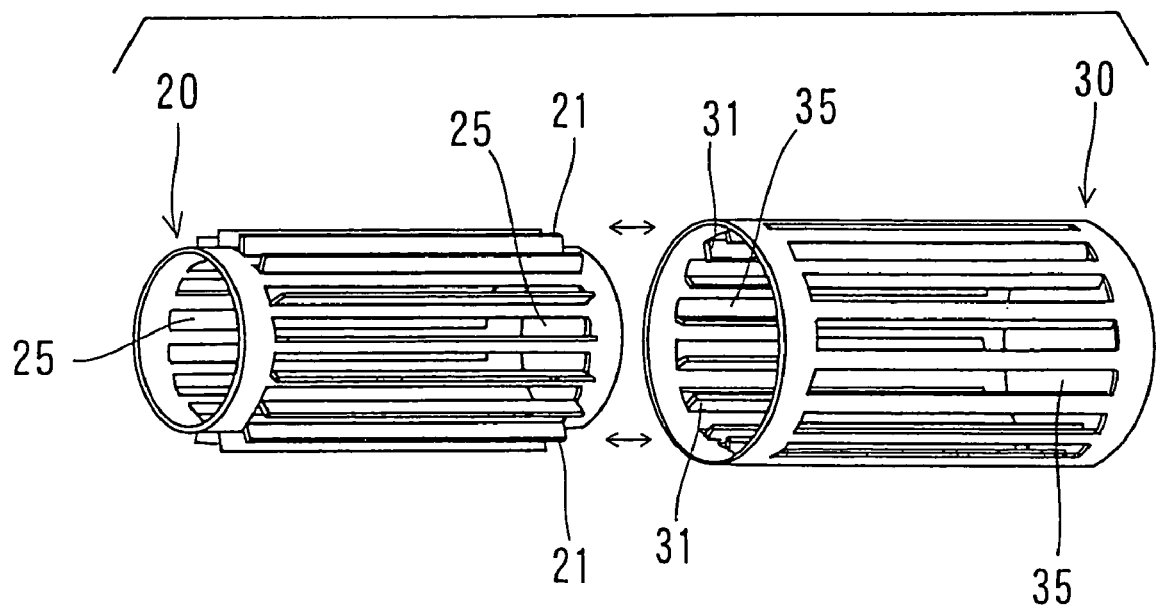
FIG. 4 is a perspective view of the oil deterioration-detecting sensor according to the embodiment.

As shown in FIGS. 3, 4, the first electrode 20 has first fins 21. The first fins 21 are protruded outwardly in a radial direction from a surface of a cylindrical body of the first electrode 20 toward the second electrode 30. The first fins 21 are extended in an axial direction of the first electrode 20.

The first fins 21 are one of protruding portions. First slits 25 are formed between adjacent first fins 21, 21, which are adjacent in a circumferential direction of the first electrode 20. The oil in the oil pan flows inside and outside the first electrode 20 through the first slits 25.

The second electrode 30 has second fins 31. The second fins 31 are protruded inwardly in the radial direction from a surface of a cylindrical body of the second electrode 30 toward the first electrode 20. The second fins 31 are extended in an axial direction of the second electrode 30. The second fins 31 are other protruding portions. Second slits 35 are formed between adjacent second fins 31, 31, which are adjacent in a circumferential direction of the second electrode 30. The oil in the oil pan flows inside and outside the second electrode 30 through the second slits 35. As a result, the oil flows through the first electrode 20 and the second electrode 30 via the first slits 25 and the second slits 35. The oil does not stay around the first electrode 20 and the second electrode 30. Therefore, the deterioration degree of the whole oil can be accurately detected.

As shown in FIG. 3, the first electrode 20 and the second electrode 30 are assembled so that two of the second fins 31, 31 are located at both sides of one of the first fins 21 and two of the first fins 21, 21 are located at both sides of one of the second fins 31. In other words, one of the first fins 21 is sandwiched between two of the second fins 31, 31. One of the second fins 31 is sandwiched between two of the first fins 21, 21.

The number of the first fins 21 is same as the number of the second fins 31. Each of the first fins 21 faces two of the second fins 31. Each of the second fins 31 faces two of the first fins 21. An outer surface of the first electrode 20 faces an inner surface of the second electrode 30 in its radial direction. As a result, it is possible to enlarge facing areas of the first electrode 20 and the second electrode 30. The interelectrode resistance Ro of the interelectrode resistor 17 between the electrodes 20, 30 is decreased as enlarging the facing areas of the electrodes 20, 30. Accordingly, it is possible to accurately detect the deterioration degree of the oil, that is, quality of the oil.

Referring to FIGS. 3, 4, each of the first fins 21 and the second fins 31 is formed by a cutting and bending process from a flat base material. Then, the base material, which has the first fins 21 or the second fins 31, is rolled to form a cylinder. After that, both edges of the rolled material are jointed by welding. As a result, the first electrode 20 and the second electrode 30 are formed.

A first angle θ21 of the first fins 21 with respect to the flat base material is formed at 90 degrees. In other words, the first angle θ21 with respect to a tangential line of the cylindrical body of the first electrode 20 is formed at 90 degrees. A second angel θ31 of the second fins 31 with respect to the flat base material is also formed at 90 degrees.

The first and second angles θ21, θ31 may be formed less than 90 degrees instead of 90 degrees. It is preferable that the angles θ21, θ31 are same. When the angles θ21, θ31 are same, the resistance Ro of the interelectrode resistor 17 can be stabilized. This is because each distance δ between the electrodes 20, 30 including the fins 21, 31 is formed in approximately same. Since each of the fins 21, 31 is formed at less than 90 degrees, the first fins 21 and the second fins 31 are not disposed too close each other. Therefore, it can be easy to install the first and second electrodes 20, 30 including the first and second fins 21, 31 to have the constant distance in the circumferential direction. In addition, when the first and second fins 21, 31 have less than 90 degrees with respect to the cylindrical body (tangential line of the cylindrical body) of the first and second electrodes 20, 30, the angels θ21, θ31 can be reduced. Therefore, it is possible to form the first and second fins 21, 31 to be resistant to cracking.

Since the first and second fins 21, 31 are formed by the cutting and bending process, the base material can be not wasted to make the fins 21, 31. This keeps facing areas of the first and second electrodes 20, 30 not to be reduced.

In this embodiment, a pair of the reference electrode and the sensitive electrode is formed with a double tube structure, which has the cylindrical shapes of the first electrode 20 and the second electrode 30. Instead of this structure, quadruple tube structure can be used as the electrodes. That is, another pair of cylindrical shapes of reference and sensitive electrodes can be installed inside the first electrode 20 or outside the second electrode 30. In such a quadruple tube structure, facing areas of the reference and sensitive electrodes can be increased in comparison with the double tube structure. When such another pair of cylindrical shapes of the reference and sensitive electrodes is installed inside the first electrode 20 that is a part of the double tube structure, the quadruple tube structure of the electrodes is not increased in size, while it is possible to enlarge the facing areas of the electrodes.

Next, a basic function of the oil deterioration detector 1 will be explained with FIG. 6.

Figure 6:
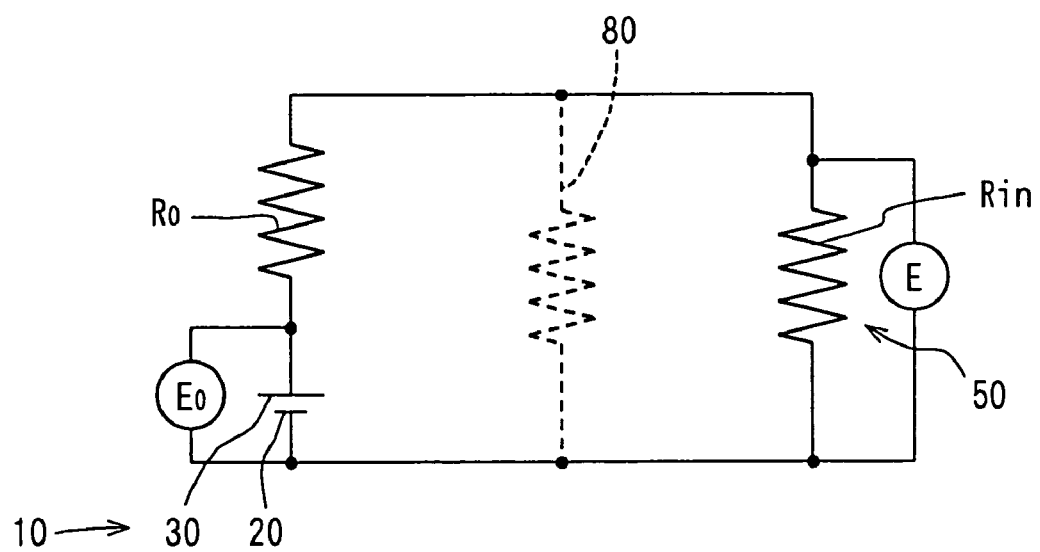
FIG. 6 is a schematic circuit diagram showing a difference between a related art and the embodiment of the present invention.

FIG. 6 is a schematic circuit diagram showing a difference between a related art and the oil deterioration detector 1 of an exemplary embodiment of the present invention. The related art has electrical components shown in FIG. 6 other than an electrical component 80 (malfunction detecting circuit) shown by a chain line. The oil deterioration detector 1 of the present embodiment has whole electrical components shown in FIG. 6 including the electrical component 80 (malfunction detecting circuit) shown by the chain line. In the oil deterioration detector 1 of the present embodiment, the malfunction detecting circuit 80 shown by the chain line is connected in parallel with the oil deterioration-detecting sensor 10 and the measurement circuit 50, if required, by the first switch 81.

At first, a radical principle of the related art will be explained.

A relation in the electric components other than the malfunction detecting circuit 80 is expressed by equations (1), (2) by using, as shown in FIG. 6, an electric potential Eo between the reference electrode 20 and the sensitive electrode 30, the interelectrode resistance Ro of the interelectrode resistor 17 between the electrodes 20 and 30, an input impedance Rin in the measurement circuit 50, and a measured electric potential E of the measurement circuit 50.

$$E/Eo = Rin/(Ro+Rin) \quad (1)$$

$$Ro = \rho \times L/S \quad (2)$$

In the equation (2), "ρ" is a volume resistivity of the oil, "L" is a distance between the electrodes, and "S" is an area of the electrodes.

As is clear from the equations (1), (2), the interelectrode resistance Ro of the interelectrode resistor 17 between the electrodes 20, 30 is a function of the distance L, the area S, and the volume resistivity ρ. This is because the first electrode 20 and the second electrode 30 are immersed in the oil, and a space between the first and second electrode 20, 30 is filled with the oil. Basically, the volume resistivity ρ of the oil is relatively high. As a result, the interelectrode resistance Ro of the interelectrode resistor 17 between the electrodes 20, 30 has a high resistance, for example, some megohm (MΩ).

It is required that the input impedance Rin of the measurement circuit 50 should be higher than the resistance Ro of the resistor 17 between the electrodes 20, 30 (Ro<Rin) so as to have an accuracy of the detection of the oil deterioration. Therefore, the measurement circuit 50 has the differential input type operational amplifier.

The oil, which is used as the hydraulic control oil and the motor oil, is changed with use in ph value. This is because foreign substances are mixed in the oil, and a characteristic of the oil is changed by an aged deterioration. The ph value indicates the acidity or basicity of the oil.

In such a constitution of the electric components, it is hard for the oil deterioration detector 1 to detect whether the sensor 10 itself malfunctions or not. This is because the characteristic of the oil is also changed with use as stated above.

In the present embodiment, the malfunction detecting circuit 80 is connected in parallel with the oil deterioration-detecting sensor 10. The malfunction detecting circuit 80 has the first switch 81 as shown in FIG. 1, as described above. Therefore, the malfunction detecting circuit 80 can be electrically conducted or not by switching the first switch 81 when necessary.

The oil deterioration detector 1 has a deterioration detecting process and a malfunction detecting process. In the deterioration detecting process, the oil deterioration detector 1 detects the deterioration of the oil. In the malfunction detecting process, the oil deterioration detector 1 detects the malfunction of the oil deterioration-detecting sensor 10.

When the deterioration detecting process is carried out in the oil deterioration detector 1, the first switch 81 is turned off. That is, the first switch 81 is electrically opened. Thus, the malfunction detecting circuit 80 is in a disconnecting condition that the circuit 80 is not electrically conducted in parallel with the oil deterioration-detecting sensor 10. Therefore, in the deterioration detecting process, the oil deterioration detector 1 has a same circuit arrangement as the related art.

On the other hand, when the malfunction detecting process is carried out in the oil deterioration detector 1, the first switch 81 is turned on. That is, the first switch 81 is electrically closed. Thus, the malfunction detecting circuit 80 is in a connecting condition that the circuit 80 is electrically conducted in parallel with the oil deterioration-detecting sensor 10 with respect to the measurement circuit 50.

In the connecting condition of the detecting circuit 80, a relation in the oil deterioration detector 1 is expressed by an equation (3), $$E/Eo = Rin/\{Ro \times (1+Rin/R1)+Rin\} \quad (3)$$

In the equation (3), whole internal resistance of the malfunction detecting circuit 80 is regarded as the resistance R1 of the first resistor 82. This is because the malfunction detecting circuit 80 has simple circuits that have the first switch 81 and the first resistor 82.

As shown in the equations (1) and (3), the measurement electric potentials E, which are output values of the measurement circuit 50, are different from each other. That is, the measurement electric potentials E are different between the disconnecting condition and the connecting condition of the malfunction detecting circuit 80. This is because, in the connecting condition, the electric potential Eo between the electrodes 20, 30 are divided between the input impedance Rin in the measurement circuit 50 and the first resistance R1 of the first resistor 82.

Hereinafter, in order to distinguish both measurement electric potentials E in the disconnecting condition and in the connecting condition, one of the measurement electric potentials E in the disconnecting condition is referred to as a normal potential Es. Similarly, the other measurement electric potential E in the connecting condition is referred to as a divided potential Ec.

In the present embodiment that has the malfunction detecting circuit 80, the malfunction condition of the sensor 10 can be determined based on a relation between the divided potential Ec and the normal potential Es.

[Detail Operation of the Present Embodiment]

Next, detail functions of the oil deterioration detector 1 of the present embodiment will be explained with FIG. 1.

The oil deterioration detector 1 operates during an operation time period. The operation time period is an entire duration in which an ignition of the vehicle is turned on, or a part of the entire duration. The operation time period has a deterioration-detecting period and a malfunction-detecting period. The deterioration-detecting period is a time duration in which the oil deterioration detector 1 evaluates the oil condition. That is, the deterioration detecting process is carried out in the malfunction-detecting period. The malfunction-detecting period is another time duration in which the oil deterioration detector 1 is permitted to check whether the oil deterioration-detecting sensor 10 malfunctions or not. That is, the malfunction detecting process is carried out in the operation time period. The deterioration-detecting period is a time period other than the deterioration-detecting period. Accordingly, both functions of the deterioration detection and the malfunction detection can be carried out by separate time periods.

[Deterioration Detecting Process]

At first, when the oil deterioration detector 1 is turned on, the deterioration-detecting period is started to carry out the deterioration detecting process. In the deterioration detecting process, the determination circuit 65 of the evaluation circuit 60 sends the deterioration detecting enabling signal at a high level ("H" level) via the first wire 61 and the third wire 63. It also sends the malfunction detecting enabling signal at a low level ("L" level) via the second wire 62.

In such a situation, the second switch 70 receives the "H" level of the deterioration detecting enabling signal via the lead wires 61, 63 and the third resistor 71. Then, the second switch 70 is turned on (closed) so that the oil deterioration-detecting sensor 10 is electrically conducted to the measurement circuit 50.

On the other hand, the inverter 67 receives the "L" level of the deterioration detecting enabling signal via the lead wire 61. The inverter 67 inverts the signal from "H" level to "L" level. The inverter 67 sends "L" level of the signal to the OR-circuit 66. The OR-circuit 66 receives "L" levels of the deterioration detecting enabling signal from the inverter 67 and the malfunction detecting enabling signal from the determination circuit 65. The OR-circuit 66 receives two "L" levels of the signals, thereby sending the "L" level of the signal to the first switch 81 of the malfunction detecting circuit 80. As a result, the first switch 81 is turned off so that the malfunction detecting circuit 80 is not conducted electrically. The first resistor 82 is not electrically conducted in parallel with the oil deterioration-detecting sensor 10.

Accordingly, the oil deterioration-detecting sensor 10 is singly and electrically conducted to the measurement circuit 50 and the evaluation circuit 60. As a result, the normal potential Es can be evaluated with the evaluation circuit 60.

Additionally, when the evaluation circuit 60 determines that the oil is deteriorated, the evaluation circuit 60 sends the deterioration signal to the display 91. The display 91 notifies the driver of the deterioration condition. Therefore, the driver can find that the oil is deteriorated.

[Malfunction Detecting Process]

In the malfunction-detecting period, in order to carry out the malfunction detecting process, the determination circuit 65 sends the deterioration detecting enabling signal at the "H" level via the first wire 61 and the third wire 63. It also sends the malfunction detecting enabling signal at the "H" level via the second wire 62. That is, in the malfunction-detecting period, the malfunction detecting enabling signal is switched from the "L" level to the "H" level.

In such a situation, the second switch 70 is maintained to conduct between the oil deterioration-detecting sensor 10 and the measurement circuit 50.

On the other hand, the OR-circuit 66 receives "H" level of the malfunction detecting enabling signal from the determination circuit 65 via the second wire 62. The OR-circuit 66 sends the "H" level of the signal to the first switch 81. As a result, the first switch 81 is turned on (closed) so that the first resistor 82 of the malfunction detecting circuit 80 is electrically conducted in parallel with the oil deterioration-detecting sensor 10.

Accordingly, the oil deterioration-detecting sensor 10 and the first resistor 82 of the malfunction detecting circuit 80 are electrically conducted to the measurement circuit 50 and the evaluation circuit 60. As a result, the divided potential Ec is evaluated by the determination circuit 65 of the evaluation circuit 60.

When the determination circuit 65 determines that the oil deterioration-detecting sensor 10 malfunctions, the determination circuit 65 sends the malfunction signal to the warning part 92. The warning part 92 notifies the driver of the malfunction condition of the oil deterioration-detecting sensor 10. Therefore, the driver can find that the oil deterioration-detecting sensor 10 malfunctions.

In addition, the malfunction-detecting period, in which the first resistor 82 is temporarily connected, is preferably limited in a short time period. The short time period is approximately minimum period, such as 10 milliseconds, to be able to measure the divided potential Ec of the measurement circuit 50 by turning the first switch 81 on.

After the malfunction-detecting period in which the divided potential Ec is stored in the determination circuit 65 of the evaluation circuit 60, the oil deterioration detector 1 is returned to the deterioration detecting process.

[Protection Process]

The measurement circuit 50 may be broken because the normal potential Es becomes greater than a normal measurement voltage under a certain malfunction condition. The certain malfunction condition may be caused with an electric short between the first electrode 20 and the second electrode 30, or a break in a wire.

Accordingly, when the determination circuit 65 determines that the oil deterioration-detecting sensor 10 malfunctions, a protection process is carried out. The protection process is carried out to prevent the measurement circuit 50 from being damaged.

In the protection process, the determination circuit 65 switches to send the deterioration detecting enabling signal at the "L" level. However, it maintains to send the malfunction detecting enabling signal at the "H" level.

In such a situation, the first switch 81 of the malfunction detecting circuit 80 is turned on. The second switch 70 is turned off. Since the second switch 70 is turned off, the connection between the oil deterioration-detecting sensor 10 and the measurement circuit 50 is not electrically conducted. That is, the connection is in an open condition.

As a result, the first resistor 82 of the malfunction detecting circuit 80 is singly and electrically conducted to the measurement circuit 50 and the evaluation circuit 60. Accordingly, the input signal of the measurement circuit 50 is defined to be ground potential via the first resistance R1 of the first resistor 82. This prevents the measurement circuit 50 from being damaged because the input voltage is limited within an allowable level of the measurement circuit 50.

According to the present embodiment, the oil deterioration detector 1 has the determination circuit 65 and the malfunction detecting circuit 80. The normal potential Es is measured in the disconnecting condition that the first switch 81 is opened so that the first resistor 82 is electrically disconnected. The divided potential Ec is measured in the connecting condition that the first switch 81 is closed so that the first resistor 82 is electrically connected in parallel with the sensor 10. Therefore, the oil deterioration detector 1 can evaluate the oil condition based on the normal potential Es. The oil deterioration detector 1 can also determine whether the oil deterioration-detecting sensor 10 malfunctions or not based on the relation between the normal potential Es and the divided potential Ec.

Figure 2:
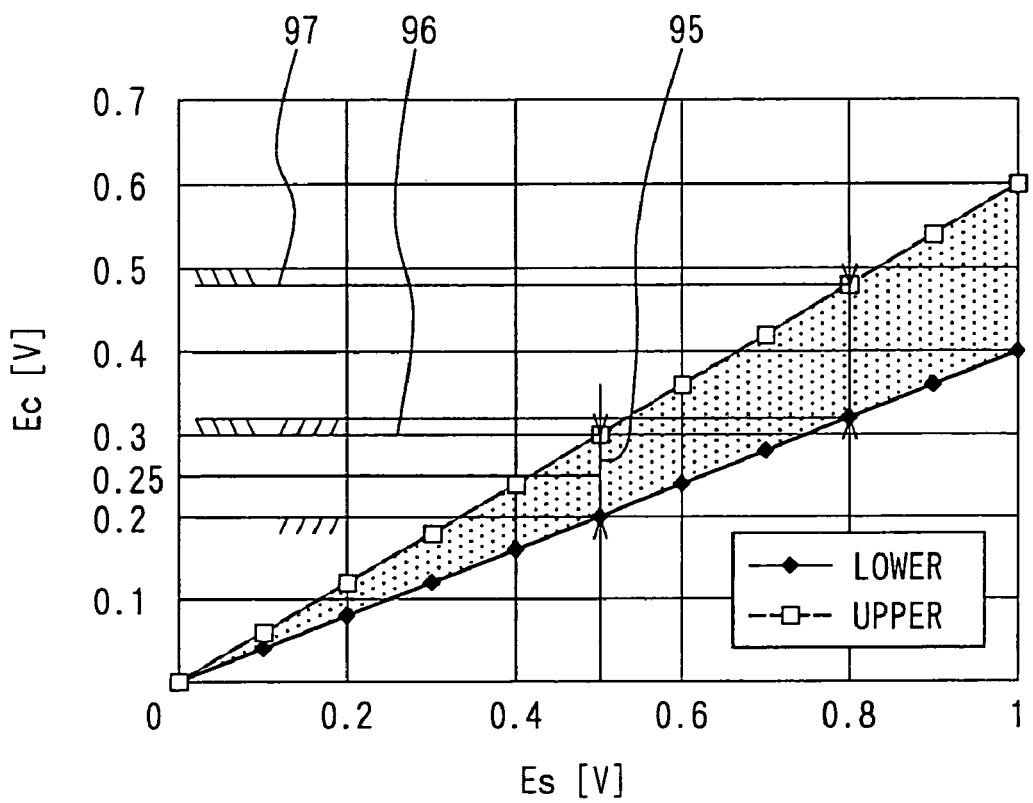
FIG. 2 is a graph showing a relation between a normal potential Es and a divided potential Ec according to the embodiment.

In detail, the relation between the divided potential Ec and the normal potential Es is shown in FIG. 2. In FIG. 2, the horizontal axis indicates the normal potential Es. The vertical axis indicates the divided potential Ec. If the relation between the divided potential Ec and the normal potential Es is not within a predetermined range 95 that is hatched in FIG. 2, the determination circuit 65 determines that the oil deterioration-detecting sensor 10 malfunctions.

For example, suppose that the interelectrode resistance Ro of the interelectrode resistor 17 is 0.5 MΩ, the first resistance R1 of the first resistance 82 is 0.5 MΩ, and the input impedance Rin of the measurement circuit 50 is an infinite (∞). In such a situation, when the normal potential Es is 0.5 volts, the divided potential Ec is 0.25 volts. When the normal potential Es is 0.8 volts due to the deterioration of the oil, the divided potential Ec is 0.4 volts. Therefore, the malfunction of the oil deterioration-detecting sensor 10 is correctly detected regardless of the oil condition.

In addition, as shown in FIG. 2, the predetermined range 95 increases as the normal potential Es increases in electric potential. For example, a first range 96 is narrower than a second range 97. The first range 96 between an upper voltage and a lower voltage is a range when the normal potential Es is equal to 0.5 volts. The second range 97 is a range when the normal potential Es is equal to 0.8 volts. The predetermined range 95 is determined in consideration of dispersion of the manufacturing. This improves accuracy of the determination of the malfunction of the oil deterioration-detecting sensor 10.

The relation between the divided potential Ec and the normal potential Es shown in FIG. 2 is stored in a memory of the determination circuit 65 with a map or a mathematical formula. Therefore, it is easy to determine whether the oil deterioration-detecting sensor 10 malfunctions or not.

According to the present embodiment, when the first switch 81 of the malfunction detecting circuit 80 is turned on so that the first resistor 82 is electrically connected in parallel with the oil deterioration-detecting sensor 10, the malfunction of the oil deterioration-detecting sensor 10 is checked. When the first switch 81 of the malfunction detecting circuit 80 is turned off so that the first resistor 82 is electrically disconnected in parallel with the oil deterioration-detecting sensor 10, the oil condition is evaluated. Therefore, the malfunction detecting process does not interfere with the deterioration detecting process of the oil condition because the first resistor 82 of the malfunction detecting circuit 80 is temporarily connected in parallel with the sensor 10 during the deterioration-detecting period.

In the present embodiment, when the determination circuit 65 determines that the oil deterioration-detecting sensor 10 malfunctions, the first resistor 82 is electrically and forcefully conducted to the measurement circuit 50 through the use of the first switch 81. This can prevent the measurement circuit 50 from being damaged without an extra protection circuit.

Further, as shown in FIG. 1, the oil deterioration detector 1 has the second switch 70 other than the first switch 81. The second switch 70 can conduct or not the connection between the oil deterioration-detecting sensor 10 and the measurement circuit 50. When the determination circuit 65 determines that the oil deterioration-detecting circuit 10 malfunctions, the second switch 70 is opened so that the oil deterioration-detecting sensor 10 is not conducted to the measurement circuit 50.

Therefore, when the oil deterioration-detecting circuit 10 malfunctions, an abnormal voltage is not applied to the amplifier 55 of the measurement circuit 50. This defines the input signal of the measurement circuit 50, and also prevents the measurement circuit 50 from being damaged.

The present invention should not be limited to the embodiments discussed above and shown in the figures, but may be implemented in various ways without departing from the spirit of the invention. For example, in the above embodiment, the predetermined range 95 between the divided potential Ec and the normal potential Es is fixed as shown in FIG. 2. Instead of the fixed range, it is preferable that the predetermined range 95 is adjustable based on the normal potential Es.

In addition, the determination circuit 65 of the evaluation circuit 60 may also determine based on whether the normal potential Es is less than a lower limit potential or more than an upper limit potential. In such a modification, if the normal potential Es is determined to be out of a certain potential range based on the limits, the determination circuit 65 determines that the oil deterioration-detecting sensor 10 malfunctions. Therefore, it is further easy to determine the malfunction of the oil deterioration-detecting sensor 10.

The determination circuit 65 may be combined in the evaluation circuit 60. In such an evaluation circuit 60, the combined evaluation circuit 60 can determine whether the oil is deteriorated, and whether the sensor 10 malfunctions without additional circuits, thereby decreasing a circuit area.

What is claimed is:

1. An oil deterioration detection apparatus comprising:
a sensor that detects a characteristic of oil and produces a characteristic signal;
a malfunction detecting circuit that has a switch connected in parallel with the sensor;
an evaluation circuit that evaluates whether the oil is deteriorated based on the characteristic signal, which is detected when the switch is opened so that the malfunction detecting circuit is not electrically conducted in parallel with the sensor; and
a determination circuit that determines whether the sensor malfunctions based on the characteristic signal, which is detected when the switch is closed so that the malfunction detecting circuit is electrically conducted in parallel with the sensor;

wherein the switch connects the malfunction detecting circuit in parallel with the sensor in a time period, and disconnects the malfunction detecting circuit from the sensor in another time period.

2. The oil deterioration detection apparatus according to claim 1, wherein the malfunction detecting circuit has a resistor, the evaluation circuit evaluates whether the oil is deteriorated based on the characteristic signal when the switch is opened so that the resistor of the malfunction detecting circuit is not electrically conducted in parallel with the sensor, and the determination circuit determines whether the sensor malfunctions based on a divided voltage in which a voltage of the characteristic signal is divided by the resistor when the switch is closed so that the resistor of the malfunction detecting circuit is electrically conducted in parallel with the sensor.

3. The oil deterioration detection apparatus according to claim 1, further comprising:

a measurement circuit having an amplifier that is electrically connected between the sensor and the evaluation circuit and the determination circuit.

4. The oil deterioration detection apparatus according to claim 3, wherein the switch is closed so that the malfunction detecting circuit is electrically conducted to the measurement circuit when the determination circuit determines that the sensor malfunctions.

5. The oil deterioration detection apparatus according to claim 4, further comprising:

a second switch that is connected between the sensor and the determination circuit so that a connection between the sensor and the determination circuit is conducted or not, wherein the second switch is opened so that the connection between the sensor and the determination circuit is not conducted when the determination circuit determines that the sensor malfunctions.

6. The oil deterioration detection apparatus according to claim 1, wherein the malfunction detecting circuit is electrically conducted in parallel with the sensor for a certain period within an operation period of the oil deterioration detection apparatus so that the determination circuit determines whether the sensor malfunctions.

7. The oil deterioration detection apparatus according to claim 1, wherein the characteristic has acidity and basicity of the oil, and the sensor outputs the characteristic signal in response to the acidity and the basicity of the oil.

8. The oil deterioration detection apparatus according to claim 1, wherein the sensor includes a reference electrode that has a constant potential regardless of acidity and basicity in the oil, and a sensitive electrode in which an electric potential changes in response to the acidity and basicity in the oil, and the sensor outputs a potential difference between the reference electrode and the sensitive electrode as the characteristic signal.

9. The oil deterioration detection apparatus according to claim 1, wherein a normal voltage is detected when the switch of the malfunction detecting circuit is opened so that the malfunction detecting circuit is not electrically conducted in parallel with the sensor, a divided voltage is detected when the switch of the malfunction detecting circuit is closed so that the malfunction detecting circuit is electrically conducted in parallel with the sensor, and the determination circuit determines whether the sensor malfunctions based on a relation between the normal voltage and the divided voltage.

10. The oil deterioration detection apparatus according to claim 9, wherein the determination circuit stores a certain range of a difference between the normal voltage and the divided voltage in advance in consideration of dispersion of a manufacturing of the sensor, and the determination circuit determines that the sensor malfunctions when the relation between the normal voltage and the divided voltage is out of the certain range.

11. The oil deterioration detection apparatus according to claim 10, wherein the certain range is adjustable based on the normal voltage.

12. The oil deterioration detection apparatus according to claim 10, wherein the certain range increases with increasing the normal voltage.

13. The oil deterioration detection apparatus according to claim 9, wherein the determination circuit determines that the sensor malfunctions when the normal voltage is less than a first threshold voltage or the normal voltage is more than a second threshold voltage that is higher than the first threshold voltage.

14. The oil deterioration detection apparatus according to claim 1, wherein the determination circuit is included in the evaluation circuit.

15. The oil deterioration detection apparatus according to claim 1, wherein the switch of the malfunction detecting circuit has a semiconductor switch.

16. A method of detecting oil deterioration, the method comprising:

detecting a characteristic of oil and producing a characteristic signal via a sensor;

providing a malfunction detecting circuit that has a switch connected in parallel with the sensor;

evaluating whether the oil is deteriorated based on the characteristic signal detected when the switch is opened so that the malfunction detecting circuit is not electrically conducted in parallel with the sensor; and determining whether the sensor malfunctions based on the characteristic signal detected when the switch is closed so that the malfunction detecting circuit is electrically conducted in parallel with the sensor;

wherein the switch connects the malfunction detecting circuit in parallel with the sensor in a time period and disconnects the malfunction detecting circuit with the sensor in a separate time period so that oil deterioration evaluation and sensor malfunction detection can be performed in separate time periods.

17. The method according to claim 16, wherein the malfunction detecting circuit has a resistor, evaluating whether the oil is deteriorated based on the characteristic signal when the switch is opened so that the resistor of the malfunction detecting circuit is not electrically conducted in parallel with the sensor, and determining whether the sensor malfunctions based on a divided voltage in which a voltage of the characteristic signal is divided by the resistor when the switch is closed so that the resistor of the malfunction detecting circuit is electrically conducted in parallel with the sensor.

18. The method according to claim 16, wherein the characteristic has acidity and basicity of the oil, and the sensor outputs the characteristic signal in response to the acidity and the basicity of the oil.

19. The method according to claim 16,
wherein the sensor includes a reference electrode that has a constant potential regardless of acidity and basicity in the oil, and a sensitive electrode in which an electric potential changes in response to the acidity and basicity in the oil, and the sensor outputs a potential difference between the reference electrode and the sensitive electrode as the characteristic signal.

20. The method according to claim 16,
wherein a normal voltage is detected when the switch of the malfunction detecting circuit is opened so that the malfunction detecting circuit is not electrically conducted in parallel with the sensor, a divided voltage is detected when the switch of the malfunction detecting circuit is closed so that the malfunction detecting circuit is electrically conducted in parallel with the sensor, and whether the sensor malfunctions is determined based on a relation between the normal voltage and the divided voltage.

* * * * *